United States Patent [19]

Klingmüller et al.

[11] Patent Number: 5,659,012

[45] Date of Patent: Aug. 19, 1997

[54] PEPTIDE WHICH BINDS $SH_2$ DOMAINS OF PROTEIN TYROSINE PHOSPHATASE SH-PTP1

[75] Inventors: Ursula Klingmüller, Arlington, Mass.; Stephen Michnick, Westmount, Canada; Benjamin G. Neel, Wayland, Mass.; Ulrike Lorenz, Boston, Mass.; Harvey F. Lodish, Brookline, Mass.

[73] Assignee: Whitehead Institute for Biomedical Research, Cambridge, Mass.

[21] Appl. No.: 402,006

[22] Filed: Mar. 10, 1995

[51] Int. Cl.$^6$ ..................... A61K 38/04
[52] U.S. Cl. ............ 530/327; 530/300; 530/350; 530/352; 530/327; 530/399; 530/345
[58] Field of Search ............ 530/300, 350, 530/352, 327, 397, 345

[56] References Cited

U.S. PATENT DOCUMENTS

| | | | |
|---|---|---|---|
| 5,278,065 | 1/1994 | D'Andrea et al. | 435/252.3 |
| 5,292,654 | 3/1994 | Yoshimura et al. | 435/240.2 |
| 5,352,660 | 10/1994 | Pawson | 514/12 |
| 5,378,808 | 1/1995 | D'Andrea et al. | 530/350 |

OTHER PUBLICATIONS

Jones et al *Blood* 76 (1990) pp. 31–35.
Burke et al *J. Org. Chem.* (1993) 58 pp. 1336–1340.
Witthuhn, Bruce A., et al., "JAK2 Associates with the Erythropoietin Receptor and Is Tryrosine Phosphorylated and Activated Following Stimulation with Erythropoietin," *Cell* 74:227–236 (1993).
Argetsinger, Lawrence S., et al., "Identification of JAK2 As a Growth Hormone Receptor–Associated Tyrosine Kinase," *Cell* 74:237–244 (1993).
Pei, Dehua, et al., "Intramolecular Regulation of Protein Tyrosine Phosphatase SH–PTP1: A New Function for Src Homology 2 Domains," *Biochemistry* 33(51):15483–15493 (1994).
Miura, Osamu, et al., "Induction of Tyrosine Phosphorylation by the Erythropoietin Receptor Correlates with Mitogenesis," *Mol. Cell Biol.* 11(10):4895–4902 (1991).
Quelle and Wojchowski, "Proliferative Action of Erythropoietin Is Associated with Rapid Protein Tyrosine Phosphorylation in Responsive B6SUt.EP Cells," *J. Biol. Chem.* 266(1):609–614 (1991).
Sonyang, Z., et al., "Specific Motifs Recognized by the SH2 Domains of Csk, 3BP2, fps/fes, GRB–2, HCP, SHC, Syk, and Vav," *Mol. Cell Biol.* 14(4):2777–2785 (1994).
D'Andrea, Alan D., et al., "Expression Cloning of the Murine Erythropoietin Receptor," *Cell* 57:277–285 (1989).
Shen, Shi–Hsiang, et al., "A Protein–Tyrosine Phosphatase with Sequence Similarity to the SH2 Domain of the Protein–Tyrosine Kinases," *Nature* 352:736–739 (1991).
Silvennoinen, Olli, et al., "Structure of the Murine Jak2 Protein–Tyrosine Kinase and Its Role in Interleukin 3 Signal Transduction," *Proc. Natl. Acad. Sci. USA* 90:8429–8433 (1993).
Sugimoto, Seiji, et al., "Activation of the SH2–Containing Protein Tyrosine Phosphatase, SH–PTP2, by Phosphotyrosine–Containing Peptides Derived from Insulin Receptor Substrate–1," *J. Biologic. Chemistry* 269(18):13614–13622 (1994).
Yi and Ihle, "Association of Hematopoietic Cell Phosphatase with c–Kit after Stimulation with c–Kit Ligand," *Mol. Cell. Biol.* 13(6):3350–3358 (1993).
Yi, Taolin, et al., "Hematopoietic Cell Phosphatase Associates with the Interleukin-3 (IL–3) Receptor β Chain and Down–Regulates IL–3–Induced Tyrosine Phosphorylation and Mitogenesis," *Mol. Cell. Biol.* 13(12):7577–7586 (1993).

*Primary Examiner*—Lora M. Green
*Assistant Examiner*—Heather A. Bakalyar
*Attorney, Agent, or Firm*—Hamilton, Brook, Smith & Reynolds, P.C.

[57] ABSTRACT

Novel assays for identifying agents which alter the effect of erythropoietin on proliferation of erythroid cells and agents identified thereby. Novel peptide comprising the erythropoietin receptor binding site for SH-PTP1.

2 Claims, 4 Drawing Sheets

SEQ ID NO: 1 → Thr-Pro-Pro-His-Leu-Lys-pTyr-Leu-Tyr-Leu-Val-Val-Ser

FIG. 4

PEPTIDE WHICH BINDS SH₂ DOMAINS OF PROTEIN TYROSINE PHOSPHATASE SH-PTP1

GOVERNMENT SUPPORT

Work described herein was supported by grant HL32262 from the National Institutes of Health. The U.S. Government has certain rights in the invention.

BACKGROUND OF THE INVENTION

Erythropoietin (EPO), a 34 kDa glycoprotein, is essential for the survival and proliferation of erythroid progenitor cells and their differentiation into erythrocytes. Like most receptors for hematopoietic growth factors, the EPO receptor (EPO-R) is a type I transmembrane protein and member of the cytokine receptor superfamily (D'Andrea et al., *Cell* 57:277–285 (1989); and D'Andrea et al., *Cell* 58:1023–4 (1989)). This superfamily includes the receptors for granulocyte-macrophage colony stimulating factor (GM-CSF), granulocyte colony stimulatory factor (G-CSF), and the interleukins IL-2, IL-3, IL-4, IL-5, IL-6 and IL-7. Binding of the ligand induces rapid but transient tyrosine phosphorylation of a number of cellular proteins, including the receptors themselves. Tyrosine phosphorylation returns to basal levels after approximately 30 minutes (Miura et al., *Mol Cell Biol* 11:4895–902 (1991)). Thus, signalling through cytokine receptors is promoted by the activation of one or more protein-tyrosine kinases (PTKs) and presumably is terminated by one or more protein-tyrosine phosphatases (PTPs). However, little is known about which specific PTPs regulate these pathways.

SUMMARY OF THE INVENTION

As described herein, SH-PTP1 specifically binds, via its SH2 domains, to an eleven amino acid peptide present in the EPO receptor which includes a phosphorylated tyrosine at amino acid residue 429 of the EPO receptor. As also described herein, SH-PTP1 specifically binds to an eleven amino acid residue peptide derived from the EPO-R amino acid sequence which includes Y429. The binding of SH-PTP1 to the EPO-R activates the phosphatase activity of SH-PTP1, resulting in dephosphorylation of the EPO receptor and the protein-tyrosine kinase JAK2 and return of the level of EPO-induced JAK2 phosphorylation to basal levels. As a result, the EPO proliferation signal is terminated.

This invention pertains to novel assays for identifying agents which alter the effect of EPO on erythroid cells. Agents identified by the assay described herein may enhance (e.g., prolong or increase) or diminish (e.g., shorten or decrease) the effect of EPO on the survival and proliferation of mature erythroid cells or erythroid progenitor cells, or may enhance or diminish the effect of EPO on the differentiation of erythroid progenitor cells into erythrocytes.

In one embodiment of the invention, an assay for identifying an agent which alters the effect of EPO on proliferation of erythroid cells comprises combining EPO, the EPO-R, the PTK JAK2, the PTP SH-PTP1 and an agent to be tested, under conditions in which binding of SH-PTP1 to the EPO-R occurs (i.e., conditions suitable for binding of SH-PTP1 to the EPO-R). Binding of SH-PTP1 to the EPO-R results in dephosphorylation of the EPO-R and JAK2 and termination of the EPO proliferative signal. The extent of proliferation of erythroid cells in the presence of an agent to be tested is determined and compared with the extent of proliferation of erythroid cells in the absence of the agent to be tested, and a difference in the extent of proliferation indicates that the agent alters the effect of EPO on erythroid cell proliferation. An increase in proliferation of erythroid cells in the presence of the agent indicates that the agent enhances, i.e., prolongs or increases, the EPO proliferative effect. A decrease in proliferation of erythroid cells in the presence of the agent indicates that the agent diminishes, i.e., shortens or decreases, the EPO proliferative effect.

This invention further pertains to novel methods of regulating the activity of a non-transmembrane protein-tyrosine kinase, comprising inhibiting the binding of a non-transmembrane protein-tyrosine phosphatase to its receptor, thereby preventing activation of the phosphatase and dephosphorylation of the protein-tyrosine kinase. In one embodiment, the receptor is selected from the receptors for EPO, granulocyte-macrophage colony stimulating factor (GM-CSF), granulocyte colony stimulating factor (G-CSF) and the interleukins IL-2, IL-3, IL-4, IL-5, IL-6 and IL-7. In another embodiment, the protein-tyrosine kinase can be JAK1, JAK2, JAK3 or TYK2. In a particular embodiment, the activity of protein kinase JAK2 is regulated by the inhibition of the binding of protein phosphatase SH-PTP1 to phosphorylated tyrosine 429 of the EPO receptor.

The present invention also relates to a method of terminating intracellular signals from a cytokine receptor comprising activating the phosphatase activity of a protein-tyrosine phosphatase through binding of the phosphatase to its corresponding binding site on the cytokine receptor, whereby the phosphatase is activated and dephosphorylates a protein-kinase, thereby terminating the intracellular signal. In a particular embodiment, the EPO proliferative signal is terminated as a result of the binding of SH-PTP1 to phosphorylated tyrosine 429 on the EPO receptor and the resulting activation of the phosphatase and dephosphorylation of the protein kinase JAK2.

The assays and methods of the present invention can be used to identify agents and drugs for use in erythrocyte proliferative disorders such as polycythemia. The assays and methods described herein can also be used to identify drugs which prolong the EPO effect and therefore can be used in any therapeutic or prophylactic application in the EPO can be used, such as for hemoglobin synthesis, or for treatment of an individual experiencing anemia associated with renal failure, chronic disease, HIV infection, blood loss or cancer. These agents or drugs act as EPO sparers or enhancers by, for example, prolonging the effects of EPO.

The present invention also relates to agents or drugs, such as, but not limited to, peptides or small organic molecules designed with reference to the site on the EPO-R shown to bind SH-PTP1. In one embodiment, such agents or drugs can be designed to mimic the activity of the EPO-R SH-PTP1 binding site in that it binds SH-PTP1; however, the drug or agent preferably will not activate the phosphatase activity of SH-PTP1. Alternatively, the drug or agent can be designed to bind to the EPO-R binding site for SM-PTP1, rendering it unavailable for binding by SH-PTP1, and thereby inhibiting the phosphatase activity of SH-PTP1. In another embodiment, the drug or agent may mimic the phosphatase activity of SH-PTP1, resulting in dephosphorylation of protein-tyrosine kinase JAK2 and termination of the EPO proliferative signal.

The EPO-R SH-PTP1 binding peptide (SEQ ID NO.: 1) can also be used as an affinity reagent to identify other phosphatases which bind the EPO-R. For instance, agents which bind to the peptide can be identified and screened for phosphatase activity.

DETAILED DESCRIPTION OF THE INVENTION

The protein-tyrosine kinase (PTK) JAK2 has been strongly implicated in signal transduction by a number of cytokine receptors (Argetsinger et al., *Cell* 74:237–244 (1993)). The EPO-R associates with JAK2, and erythropoietin binding to the EPO-R specifically but transiently increases JAK2 autophosphorylation and kinase activity (Witthuhn et al., *Cell* 74:227–236 (1993)).

In many growth factor receptors, phosphotyrosine (pY) residues serve as docking sites for proteins involved in downstream signal propagation. These secondary signaling molecules, such as phospholipase Cγ (Meisenhelder et al., *Cell* 57:1109–1122 (1989)), ras GTPase activating protein (GAP; Kaplan et al., *Cell* 61:125–133 (1990)) and the regulatory subunit of phosphatidylinositol 3-kinase (Cantley et al., *Cell* 64:281–302 (1991)), contain src homology 2 (SH2) domains. SH2 domains comprise approximately 100 amino acid residues that selectively bind with high affinity to pY residues within specific amino acid sequences (Cantley et al., 1991).

Although termination of signals generated by PTKs most likely involves tyrosine dephosphorylation, little is known about which specific protein-tyrosine phosphatases (PTPs) regulate these pathways. The identification of a subclass of nontransmembrane PTPs which contain SH2 domains suggests a role for these phosphatases in signaling from activated receptors. SH-PTP2 (Syp, PTP1D, PTP2C) the homolog of Drosophila corkscrew, is ubiquitously expressed (Freeman, Jr. et al., *PNAS* 89:11239–11243 (1992)) and binds via its SH2 domains to several growth factor receptors (Feng et al., *Science* 259:1607–1611 (1993)). Recent studies suggest that SH-PTP2 is a positive signal transducer in some receptor protein-tyrosine kinase pathways (Li et al., *Mol Cell Biol* 14:509–517 (1994)).

Conversely, SH-PTP1 appears to be a negative regulator of growth factor signaling. Unlike SH-PTP2, SH-PTP1 is expressed predominantly in hematopoietic cells, although it is also detected in some epithelial cells (Shen et al., *Nature* 352:736–739 (1991)). The work described herein shows that SH-PTP1 binds selectively to phosphotyrosine 429 in the cytoplasmic domain of the EPO-R. This interaction mediates the dephosphorylation and inactivation of JAK2. It has also been shown that an 11 amino acid peptide corresponding to the segment surrounding phosphotyrosine 429 directly activates the phosphatase activity of SH-PTP1 (Pei et al., *Biochemistry*, 33(51):15483–15493 (1994)). Recruitment of SH-PTP1 to phosphotyrosine Y429 of the EPO-R, induced by EPO binding, causes dephosphorylation of JAK2. Since stable expression of the Y429F mutant EPO-R allows proliferation of cells in one-fifth to one-tenth the concentration of EPO required for cells expressing wild-type EPO-R, SH-PTP1-induces modulation of signals generated by the activated erythropoietin receptor.

SH-PTP1 Associates With the EPO-R After EPO Addition

To study proteins involved in EPO-R signaling, the wild-type (wt) and mutant EPO-Rs were expressed in the pro-B cell line Ba/F3. In agreement with previous results (Miura, et al., *Mol Cell Biol* 11:4895–902 (1991); Quelle and Wojchowski, *J Biol Chem* 266:609–614 (1991)), the addition of EPO to transfected cells expressing the wt EPO-R induced receptor phosphorylation at one or more tyrosine residues, as demonstrated by immunoblotting with the anti-phosphotyrosine monoclonal antibody 4G10 (anti-PTyr). Tyrosine phosphorylation of the EPO-R is transient and returns to basal levels within 60 minutes (Dusanter-Four, et al., *J Biol Chem* 267:10670–10675 (1992); Linnekin, et al., *PNAS* 89:6237–6241 (1992)), indicating that a phosphotyrosine phosphatase may be recruited to the receptor.

Since SH-PTP1 is expressed in hematopoietic cells, including Ba/F3, it was investigated whether SH-PTP1 associates with the EPO-R. Co-immunoprecipitation experiments showed a specific interaction between the EPO-R and SH-PTP1. Ba/F3 cells expressing the wt EPO-R were either stimulated for 5 minutes with 100 units/ml EPO or left unstimulated. Detergent lysates of these cells were prepared and used for immunoprecipitation experiments. Analysis of anti-SH-PTP1 immunoprecipitates by immunoblotting with anti-PTyr and reprobing with a polyclonal antiserum against SH-PTP1 revealed a low basal level of tyrosine phosphorylation of SH-PTP1. In both control cells and cells expressing the EPO-R, the extent of tyrosine phosphorylation of SH-PTP1 was unchanged upon EPO addition. This was confirmed by metabolic labeling with $^{32}$PO4 and phosphoamino acid analysis. In Ba/F3 cells expressing the wt EPO-R and stimulated with EPO, the anti-SH-PTP1 antiserum also immunoprecipitated a tyrosine-phosphorylated protein which migrated with an apparent molecular weight of 75 kDa, and co-migrated with the tyrosine-phosphorylated EPO-R. This protein was absent in SH-PTP1 immunoprecipitates from lysates of parental Ba/F3 cells and was not precipitated by matched pre-immune serum, suggesting that it might be the tyrosine-phosphorylated EPO-R. To determine whether the 75 kDa SH-PTP1-associated protein was the EPO-R, anti-SH-PTP1 immunoprecipitates from lysates of cells expressing the wt EPO-R and stimulated with EPO were treated with 1% SDS and then denatured. Upon re-immunoprecipitation with anti-EPO-R antiserum the 75 kDa tyrosine-phosphorylated protein could be detected by anti-PTyr immunoblotting. Tyrosine phosphorylated SH-PTP1 was not recovered in the second immunoprecipitation, indicating that the association of SH-PTP1 with the EPO-R was disrupted by the heat treatment. Thus, several lines of evidence suggest that the 75 kDa tyrosine phosphorylated protein complexed, after EPO addition, with SH-PTP1 is the tyrosine phosphorylated EPO-R: (i) it was re-immunoprecipitated with anti-EPO-R antiserum; (ii) it was absent in the anti-SH-PTP1 immunoprecipitate from extracts of parental Ba/F3 cells; and (iii) it was reduced in size upon deletion of the 40 C-terminal amino acids of the EPO-R. The tyrosine phosphorylated EPO-R could not be detected directly by immunoblotting with the anti-EPO-R antiserum. One reason for this finding is that the sensitivity of the anti-PTyr monoclonal antibody is greater than that of the anti-EPO-R antibodies. Another reason is that only a small fraction of the EPO-R molecules—approximately 1000 receptors per cell—is present at the cell surface.

Thus, in response to EPO, the wt EPO-R becomes tyrosine-phosphorylated and forms a complex with SH-PTP1. SH-PTP1 was not detected in anti-EPO-R immunoprecipitates, probably because only a small fraction of the tyrosine-phosphorylated EPO-R associates with SH-PTP1 at any given time. These experiments did not determine whether unphosphorylated EPO-R, before EPO addition, is complexed with SH-PTP1. However, the finding (below) that SH-PTP1 binding requires a specific phosphotyrosine in the EPO-R and is mediated by the SH2 domains of SH-PTP1 makes this unlikely, suggesting that SH-PTP1 associates with the EPO-R only after ligand-induced tyrosine phosphorylation of the receptor.

Phosphotyrosine 429 in the Cytoplasmic Domain of the EPO-R Mediates Binding of SH-PTP1

Figure 1:
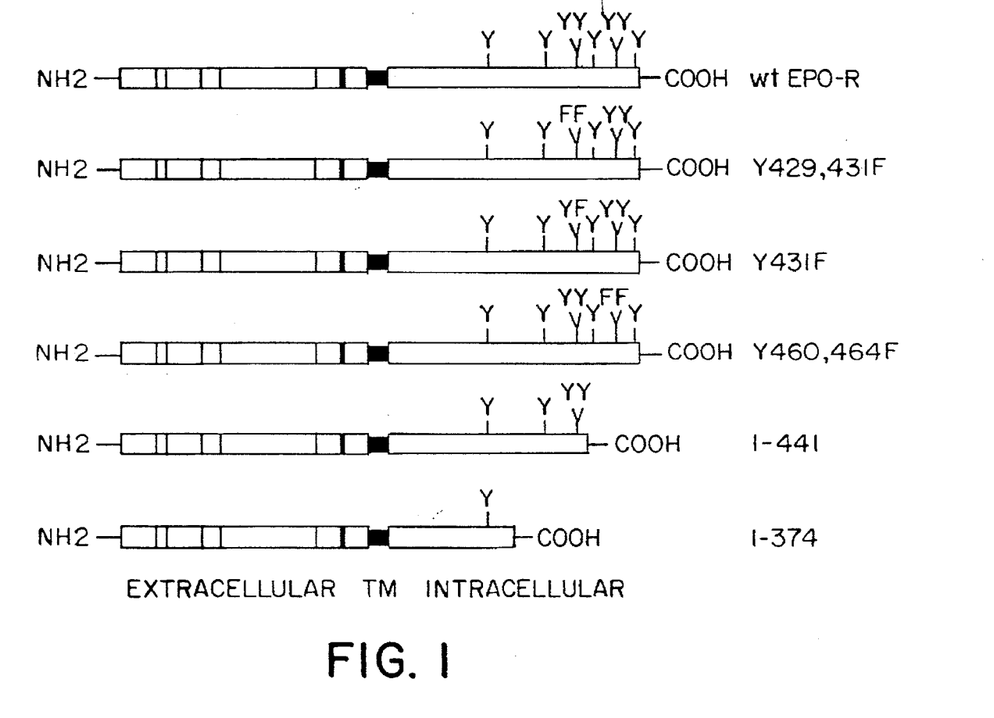
FIG. 1 is a schematic diagram of mutant EPO-Rs. Open boxes symbolize the extracellular and intracellular domains of the EPO-R. Vertical lines in the extracellular domain represent conserved cysteine residues and the filled box the WSXWS motif. The transmembrane domain (TM) is symbolized by a filled black box. The mutant EPO-Rs are named either according to the amino acid position of the tyrosine (Y) exchanged to phenylalanine (F) or the last amino acid expressed in the deleted EPO-R.

To determine which amino acid in the cytosolic domain of the EPO-R is responsible for binding SH-PTP1, a panel of EPO-R deletion and tyrosine (Y) to phenylalanine (F) point mutants was generated (shown schematically in FIG. 1). To obtain stable cell lines, normally In-3 dependent Ba/F3 cells were transfected with plasmids harboring the altered EPO-R cDNAs. Pools of cells were selected initially in G418 and IL3. Each of these EPO-R mutants gave rise to a comparable number of cell pools that were able to grow with EPO as the sole added growth factor. Thus, none of the altered tyrosine residues nor the approximately 100 C-terminal amino acids of the EPO-R was essential for the generation of a proliferative signal in Ba/F3 cells.

Immunoprecipitation of cell lysates with anti-EPO-R antiserum, followed by anti-PTyr immunoblotting, showed that all of the mutant receptors tested in this experiment became tyrosine phosphorylated after EPO addition. EPO-induced tyrosine phosphorylation of the C-terminal deletion mutant 1-374 could not be detected. All point mutants except Y429,431F generated a tyrosine phosphorylated EPO-R with the same gel mobility as the wt EPO-R. Reproducibly, the tyrosine phosphorylated mutant Y429,431F migrated as a diffuse species somewhat slower that the wt EPO-R. The altered gel mobility could be due to tyrosine phosphorylation on new sites or higher occupancy of the same sites phosphorylated in the wt EPO-R (or both). Of the 8 tyrosine residues in the EPO-R cytoplasmic domain, 4 are deleted in the C-terminal truncated mutant EPO-R 1-441. Nonetheless, this receptor also becomes tyrosine-phosphorylated. That all of the mutant receptors containing Y to F mutations or a deletion of the C-terminal 40 amino acids became tyrosine-phosphorylated after EPO addition suggested either that the target tyrosine for phosphorylation had not been altered or, more likely, that the cytosolic domain of the EPO-R has multiple tyrosine phosphorylation sites.

The finding that SH-PTP1 associates with tyrosine-phosphorylated wt EPO-R suggested that one or more tyrosine residues in the cytosolic domain of the EPO-R could be crucial for binding. The ability of the mutant EPO-Rs to form a complex with SH-PTP1 was analyzed by co-immunoprecipitation. In Ba/F3 cells expressing EPO-R 1-441, a tyrosine-phosphorylated protein of approximately 68 kDa co-immunoprecipitated with SH-PTP1. This protein represented the truncated 1-441 EPO-R because: (i) it co-migrated with the tyrosine-phosphorylated EPO-R 1-441; (ii) it was not precipitated from parental Ba/F3 cells or cells expressing the wt EPO-R; and (iii) it was absent in immunoprecipitates with pre-immune serum. The C-terminal 40 amino acids of the EPO-R, previously identified as a negative regulatory domain (D'Andrea, et al., *Mol Cell Biol* 11:1980–1987 (1991); Yoshimura and Lodish, *Mol Cell Biol* 12:706–715 (1992)), thus are not required for interaction with SH-PTP1. This result eliminates the 4 tyrosine residues in the C-terminal segment as essential docking sites for SH-PTP1.

Similar experiments showed that the tyrosine-phosphorylated forms of all of the EPO-Rs with point mutations, except Y429,431F, become complexed with SH-PTP1 after EPO addition. Proteins from lysates of EPO-stimulated cells were immunoprecipitated either with anti-SH-PTP1 or anti-EPO-R antibodies and were analyzed by anti-PTyr immunoblotting. The mutant receptors Y429, 431F and Y460, 464F were tyrosine phosphorylated to similar extents as the wt EPO-R. However, only the tyrosine-phosphorylated wt and Y460, 464F receptors co-immunoprecipitated with SH-PTP1. Since the Y431F receptor became tyrosine phosphorylated and complexed with SH-PTP1 (see below) after EPO addition, these results suggest that Y429 becomes phosphorylated after EPO addition, and serves as the docking site for an SH2 domain in SH-PTP-1.

SH-PTP1 Binds via Its SH2 Domains to the EPO-R

To investigate whether the SM2 domains of SH-PTP1 mediate binding to the EPO-R, glutathione S-transferase (GST) fusion proteins containing both SH2 domains of SH-PTP1 (GST-N+C-SH2) or only the N-terminal SH2 domain (GST-N-SH2) were produced in bacteria, bound to glutathione-agarose beads, and incubated with lysates from EPO-stimulated Ba/F3 cells expressing wt EPO-R or EPO-R mutants. Bound tyrosine-phosphorylated proteins were revealed by anti-PTyr immunoblotting. Control immunoprecipitations from the same lysates using the anti-EPO-R antibody and anti-PTyr immunoblotting revealed that, as before, all receptors were tyrosine-phosphorylated to a similar extent after EPO addition. The wt EPO-R bound specifically to GST-N+C, but not to GST alone. Mutation of EPO-R Y461 or Y464 had no effect on GST-N+C binding. However, the double point mutant Y429,Y431F did not bind to GST-N+C, suggesting that either Y429 and/or Y431 was required for binding. Since the point mutant Y431F bound to GST-N+C, it was concluded that Y429 is the major binding site for SH-PTP1 on the EPO-R. The same qualitative pattern of selective binding was obtained with the GST fusion protein containing only the N-terminal SH-PTP1 SH2 domain. However, the amount of tyrosine-phosphorylated EPO-R bound to GST-N-SH2 was much lower. The N-terminal SH-PTP1 SH2 domain without the C-terminal SH2 domain could have a reduced affinity for tyrosine-phosphorylated Y429, or the N-terminal SH2 domain of SH-PTP1, when expressed without the other SH2 domain, might be improperly folded. Thus, the N-terminal SM2 domain of SH-PTP1 is sufficient to bind specifically the tyrosine-phosphorylated cytosolic domain of the wt EPO-R.

Taken together with work described herein, these results show that the SH2 domains of SH-PTP1 mediate binding to phosphotyrosine 429 in the cytosolic domain of the EPO-R.

Recruitment of SH-PTP1 to the EPO-R Causes Dephosphorylation of JAK2

In a separate study (D. Pei et al., *Biochemistry*, 33(51):15483–15493 (1994)) it was demonstrated that a phosphotyrosine-containing peptide corresponding to the sequence surrounding Y429 in the EPO-R directly bound to the N-terminal SH2 domain of SH-PTP1 and activated its enzymatic activity. Thus, binding of SH-PTP1 to the activated EPO-R would be expected to localize SH-PTP1 adjacent to possible targets for dephosphorylation. One obvious potential target is JAK2, as it becomes transiently tyrosine phosphorylated after EPO addition (Witthuhn, et al., Cell 74:227–236 (1993)).

Binding of SH-PTP1 to the EPO-R causes dephosphorylation of JAK2, as shown by the immunoprecipitation experiments described below. For these experiments and the proliferation experiments described below, the wt EPO-R and the EPO-R mutants were expressed in the myeloid cell line 32D. Unlike BaF3 cells, which are aneuploid and spontaneously can give rise to factor-independent variants, parental 32D cells are diploid and rigorously IL3-dependent (Metcalf, Blood 65:357–62 (1981); Migliaccio, et al., *J Cell Biol* 109:833–841 (1989)). Although Ba/F3 cells facilitate biochemical studies of the EPO-R, cell lines like 32D might reflect the in vivo situation more closely. 32D cells expressing either the wt EPO-R or the EPO-R mutants Y429,431F or 1–374 were lysed at various times after EPO-R addition, then subjected to anti-JAK2 immunoprecipitation followed by anti-PTyr immunoblotting. As a control for equal recovery of JAK2 in the immunoprecipitates, the blot was reprobed with anti-JAK2 antiserum. In cells expressing the wt EPO-R, tyrosine phosphorylation of JAK2 was maximal at 5 minutes after EPO addition and then declined, reaching basal levels 45 minutes post-stimulation. In contrast, in cell pools expressing the mutant EPO-R Y429,431F or the truncated EPO-R 1-374, the extent of JAK2 phosphorylation was enhanced and phosphorylation persisted for at least 60 min. after EPO addition. Quantitation of these results revealed that the half life of JAK2 tyrosine-phosphorylation in cells expressing the wt EPO-R was approximately 18 minutes. In contrast, in two independent cell pools expressing the Y429,431F EPO-R, tyrosine-phosphorylation of JAK2 was only marginally reduced from the maximum value after 60 minutes of EPO treatment. Thus, binding of SH-PTP1 to the cytosolic domain of the EPO-R and its presumed subsequent activation—processes abrogated by the Y429F mutation or a deletion including Y429—are required for prompt dephosphorylation of JAK2.

SM-PTP1 Causes Dephosphorylation and Inactivation of JAK2

The downregulation of JAK2 by SH-PTP1 can be reconstituted in an insect cell system. In these studies Sf9 cells were infected by a baculovirus encoding JAK2 alone or together with baculoviruses encoding either SH-PTP1 or its close relative SH-PTP2. Overexpression of JAK2 in Sf9 cells resulted in extensive JAK2 tyrosine phosphorylation as judged by anti-PTyr immunoblotting of total cell lysates. Co-expression of SH-PTP1 greatly reduced the extent of JAK2 phosphorylation, whereas co-expression of SH-PTP2 had minimal effect. The amount of JAK2 protein expressed was not significantly affected by co-expression of the phosphatases. Analysis of cell lysates by Coomassie blue staining showed that both Sh-PTP1 and SH-PTP2 were expressed at similar levels. The overall phosphatase activity of the expressed SH-PTP1 and Sh-PTP2 proteins also was comparable, as the tyrosine phosphorylation of a group of proteins between 70 kDa and 105 kDa is similarly reduced in lysates of cells expressing SH-PTP1 or SH-PTP2. Lysates from cells expressing SH-PTP1 and Sh-PTP2 were also equivalent in their ability to dephosphorylate an exogenous peptide substrate (data not shown). These findings further support the theory that JAK2 is specifically dephosphorylated by SH-PTP1 in vivo.

To determine whether dephosphorylation influenced the kinase activity of JAK2, JAK2 was immunoprecipitated from SF9 cells expressing JAK2 alone or together with SH-PTP1 or SH-PTP2, and kinase activity was measured using a GST-EPO-R cytoplasmic domain fusion protein as an exogenous substrate. As revealed by anti-PTyr immunoblotting of the kinase reaction products, JAK2 efficiently phosphorylated the GST-EPO-R fusion protein. Co-expression of SH-PTP1 with JAK2 strongly inhibited JAK2 kinase activity; co-expression of SH-PTP2 with JAK2 again had no effect. These data suggest that similar deactivation of JAK2 occurs in transfected 32D cells when SH-PTP1 becomes bound to the tyrosine-phosphorylated EPO-R after addition of EPO.

Figure 2:
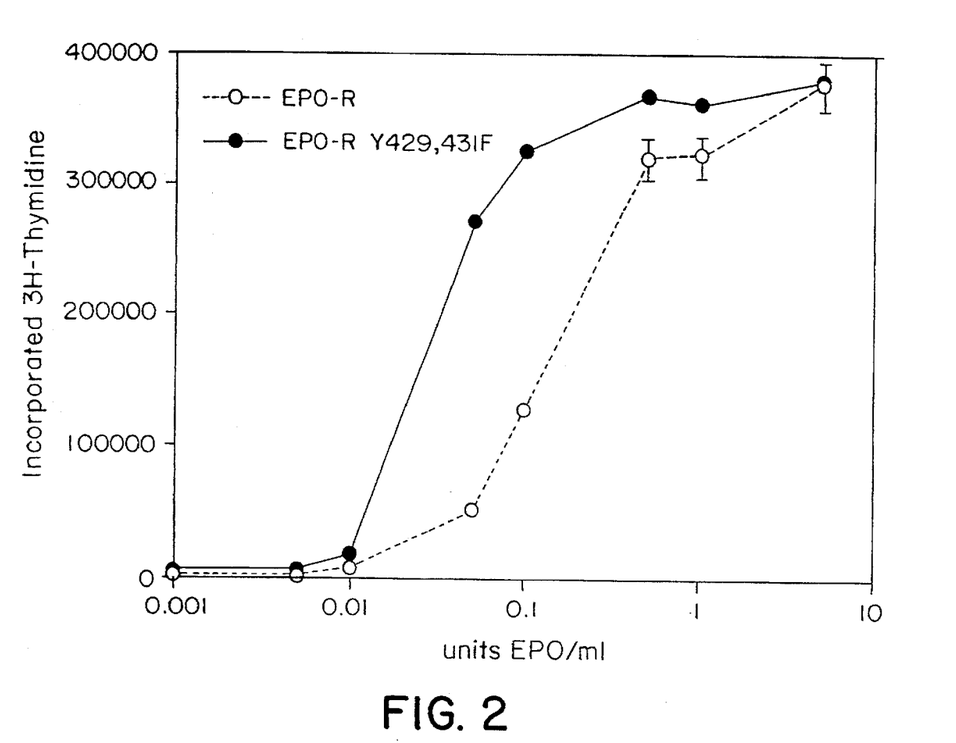
FIG. 2 is a graphic illustration of EPO-dependent proliferation of 32D cells expressing the wt EPO-R and the EPO-R mutant Y429, 431F. The graph shows the proliferation of one representative out of six independent cell pools—expressing the wt EPO-R or the EPO-R mutant Y429, 431F—in the presence of 0–5 units EPO/ml measured by $^3$H-Thymidine incorporation. Each data point represents the mean of triplicate determinations±standard deviation.

32D Cells Expressing an EPO-R Unable to Bind SH-PTP1 are Hypersensitive to EPO To assess the role of SH-PTP1 in regulating proliferative signals generated by the EPO-R, the proliferation of 32D cells expressing wt EPO-R or EPO-R Y429,431F was measured. All cell pools analyzed showed comparable growth rates in IL 3 and expressed the same number of cell-surface EPO receptors. When grown in EPO, the half-maximal proliferation of pools of 32D cells expressing the wt EPO-R, the half-maximal proliferation of pools of 32D cells expressing the wt EPO-R required 0.25 units EPO/ml and maximal proliferation required about 1 units/ml (FIG. 2). In contrast, although proliferation of EPO-R Y429,431F-expressing cells remained EPO-dependent, 6 of 6 independent cell pools expressing the mutant receptors displayed a leftward shift in the EPO dose-responsive curve. Pools of 32D cells expressing the mutant EPO-R Y429,431F achieved half-maximal proliferation in as little as 0.025 units EPO/ml, reaching a maximum rate at 0.1 units/ml (FIG. 2). At the highest EPO concentrations employed, the rate of proliferation of cell pools expressing the wt EPO-R or the EPO-R mutant Y429,431F was the same. Thus, expression of an EPO-R unable to bind SH-PTP1 allows cells to proliferate in one-fifth to one-tenth the normal amount of EPO, indicating that the recruitment of SH-PTP1 to the EPO-R is important for down-modulation of intracellular signaling through the EPO-R.

Binding of ligand to members of the cytokine receptor superfamily induces the tyrosine phosphorylation of several proteins including the receptors themselves. Since phosphorylation is transient, presumably PTP's cause protein dephosphorylation and signal termination. The first high affinity binding site for a specific PTP within the cytoplasmic domain of a cytokine receptor has been identified as described herein. SH-PTP1 specifically binds, via its SH2 domains, to phosphotyrosine 429 in the cytoplasmic domain of the EPO-R. This association requires binding of EPO to the receptor, indicating that SH-PTP1 is selectively recruited to the activated signaling complex. Binding of SH-PTP1 to phosphotyrosine 429 activates SH-PTP1 enzymatic activity (D. Pei, et al., *Biochemistry*, 33(51):15483–15493 (1994)) and causes dephosphorylation and inactivation of JAK2 kinase. The latter event was reconstituted in an insect cell system, where expression of SH-PTP1 but not its close relative SH-PTP2 leads to specific JAK2 dephosphorylation and inactivation of its kinase activity. Most importantly, activation of SH-PTP1 by binding to the EPO-R is essential for appropriate down-modulation of intracellular proliferative signals, since cells expressing mutant EPO-Rs that are unable to bind SH-PTP1 (Y429,431F and 1-374) display prolonged JAK2 activation. This allows such cells to proliferate in one-fifth to one-tenth the concentration of EPO required cells expressing the wild type EPO-R.

The binding specificity of the SH2 domains of SH-PTP1 has been an open question. In vitro binding studies using a degenerate phosphotyrosyl peptide library showed that the SH2 domains of SH-PTP1 bind to phosphopeptides with the general sequence motif phosphotyrosine-hydrophobic-Xxx-hydrophobic, where Xxx can be an amino acid. The preferred amino acids at positions +1 and +3 in the target sequence for the Sh-PTP1 SH2 domains were reported to be phenylalanine (Songyang, et al., *Mol Cell Biol* 14:2777–2785 (1994)). According to this prediction, upon phosphorylation five of the eight tyrosine residues in the cytosolic domain of the EPO-R (residues Y343, Y401, Y429, T432 and Y479) might bind SH-PTP1.

The association of SH-PTP1 with wild-type and mutant EPO-Rs expressed in transfected Ba/F3 cells was measured, as well as the association in vitro of purified SH2 domains of SH-PTP1 with the tyrosine-phosphorylated cytosolic domains of wild-type and mutant EPO-Rs. Both studies showed that Y429 in the EPO-R is essential for binding to SH-PTP1. Using synthetic peptides, it was shown that only phosphotyrosine 429, in the sequence phosphotyrosine-Leu-Tyr-Leu-Val-Val, is capable of binding SH-PTP1. A phosphopeptide containing the sequence corresponding to this segment of the EPO-R specifically binds the N-terminal SH2 domain of SH-PTP1 and activates the phosphatase activity (D. Pei, *Biochemistry*, 33(51):15483–15493 (1994)). By analogy to results of phosphotyrosyl peptide competition assays performed on SH-PTP2 (Case, et al., *J Biol Chem* 269:10467–10474 (1994)), and the recent solution of the crystal structure of the SH-PTP2 N-terminal SH2 domains for phosphotyrosyl peptides is also influenced by the amino acid residues at the +4 and +5 positions from the target phosphotyrosine. The role of these residues (433 and 434) in the EPO-R has not yet been studied. Interestingly, other cytokine receptors reported to form complexes with SH-PTP1, (e.g., c-Kit and the IL 3 receptor β chain) contain sequences resembling the SH-PTP1 binding site in the EPO-R.

Identification of Y429 as the binding site for SH-PTP1 in the EPO-R allowed the examination of the physiological role of association of SH-PTP1 with the EPO-R. At least one function of receptor-associated SH-PTP1 appears to be the dephosphorylation and inactivation of JAK2. Most likely, JAK2 is a direct substrate of SH-PTP1, a contention supported by the results of the insect cell reconstitution studies. The results thus identify the first PTK substrate of a non-transmembrane PTP. Previous studies have established that the transmembrane PTPs CD45 (Trowbridge and Thomas, 1994) and HPTPa (den Hertog, et. al., *EMBO J* 12:3789–3798 (1993)) dephosphorylate the negative regulatory tyrosines of members of the src subfamily of non-transmembrane PTKs, resulting in PTK activation. Conversely, SH-PTP1-mediated dephosphorylation of JAK2 results in JAK2 inactivation.

Binding of SH-PTP1 to other cytokine receptors probably would have similar consequences. As the IL receptor β chain has been reported to activate JAK2 (Silvennoinen, et al., *PNAS* 90:8429–8433 (1993)) and to associate with SH-PTP1 (Yi, et al., *Mol Cell Biol* 13:7577–7586 (1993)), it is likely that signaling through this receptor is regulated in a similar fashion as the EPO-R. Yi, et al., (1993) reported that DA-3 cells with decreased SH-PTP1 protein levels due to the expression of antisense SH-PTP1 show hyperphosphorylation of the IL3 receptor β chain and a slight increase in proliferation in response to IL3, and suggested that the IL3 receptor β chain is a direct SH-PTP1 target. However, in the context of the results described herein, it is unclear whether the IL3 receptor β chain hyperphosphorylation observed by Yi, et al. was due to decreased dephosphorylation by SH-PTP1 or instead was a secondary consequence of prolonged JAK2 activation. EPO-Rs mutated at Y429 also have altered gel mobilities suggestive of additional phosphorylated tyrosine residues. It will be important to determine whether SH-PTP1 dephosphorylates one or more of these sites. Furthermore, it should be noted that whereas Yi, et al. studies the effect of decreasing the total level of SH-PTP1 expression within a cell, the studies described herein focus on the specific role of receptor-bound SH-PTP1. This may account for the profound enhancement of cytokine sensitivity observed.

Cells expressing EPO-Rs incapable of SH-PTP1 binding manifest prolonged JAK2 activation. As JAK2 kinase is believed to be crucial for the generation of a proliferative signal by the EPO-R (Witthuhn, et al., *Cell* 74:227–236 (1993)), it was speculated that the extended activity of JAK2 would alter the growth properties of these cells. Indeed, such cells proliferate in EPO concentrations five-fold to ten-fold lower than the 0.5 to 1 units/ml of EPO normally required for proliferation of cells expressing the wt EPO-R. The theory that abnormal JAK2 regulation and hyperproliferation are causally related is supported by recent studies in Drosophila. A mutation in the hopscotch locus, which encodes a JAK kinase homolog, that generates a constitutively active JAK kinase results in hematopoietic tumors (Hanratty and Dearolf, *Mol Genet* 238:33–37 (1993)).

The results described herein provide a molecular explanation for the hypersensitivity of erythroid precursor cells to erythropoietin observed in two genetic syndromes. In mice, a central role for SH-PTP1 in EPO-R signaling was suggested by studies of mice that either lack SH-PTP1 (motheaten) or are impaired in SH-PTP1 phosphatase activity (motheaten viable). The CFU-E erythroid progenitors from these mice are stimulated by lower than normal concentrations of EPO, and there are increased numbers of splenic CFU-Es in vivo (van Zant and Shultz, *Exp Hematol* 17:81–87 (1989)). A possible explanation for these observations is that occupancy by EPO of fewer than normal cell surface EPO-Rs is sufficient to generate a proliferative signal, and that SH-PTP1 is an important down modulator of EPO-R signaling. However, it was also conceivable that the enhanced sensitivity of motheaten CFU-Es to EPO results from dysregulation of another signal transduction pathway that served to lower the threshold for EPO-R stimulation. The results described herein clearly establish that SH-PTP1 is a direct regulator of EPO receptor signaling.

Members of a large Finnish family with autosomal dominant benign erythrocytosis have a mutation in one allele of the EPO-R, which introduces a premature stop codon and generates an EPO-R lacking the carboxy-terminal 70 amino acids (de la Chapelle, et al., *PNAS* 90:4495–4499 (1993)). This deleted segment includes the binding site for SH-PTP1 defined herein in the murine EPO-R. The only pathophysiologic manifestation of this trait is a high hematocrit and a corresponding increase in the concentration of hemoglobin in the blood. Similar to the erythroid progenitors from motheaten mice, cultured erythroid progenitors from these patients are stimulated by lower than normal concentrations of EPO. The inability of SH-PTP1 to bind to the truncated EPO-R or to be activated could account for the enhanced responsiveness of these cells to EPO. Therefore, it will be of great interest to address whether polycythemia syndromes are also caused by an alteration in the EPO-R or an impairment of SH-PTP1 or its regulation.

At present the possibility cannot be ruled out that, besides SH-PTP1, other proteins down modulate signal transduction by the EPO-R. Even in cell lines expressing mutant EPO-Rx that are unable to associate with SH-PTP1, EPO-induced JAK2 phosphorylation eventually declines, suggesting that other PTPs can dephosphorylate JAK2. Additionally, expression in Ba/F3 cells of EPO-R 1-441, deleted for the C-terminal 40 amino acids, allows proliferation in lower than normal EPO concentrations (D'Andrea, et al., *Mol Cell Biol* 11:1980–1987 (1991); Yoshimura and Lodish, 1992). The present studies showed that EPO-R 1-441 is phosphorylated after EPO addition and that the phosphorylated truncated receptor binds SH-PTP1 normally. Presumably SH-PTP1 is activated by binding to the 1-441 receptor. Similarly, mutation Y460,464F had no effect on receptor phosphorylation or on binding to SH-PTP1. It is possible that some other down-modulatory proteins bind to the C-terminal 40 amino acids of the EPO-R.

Figure 3:
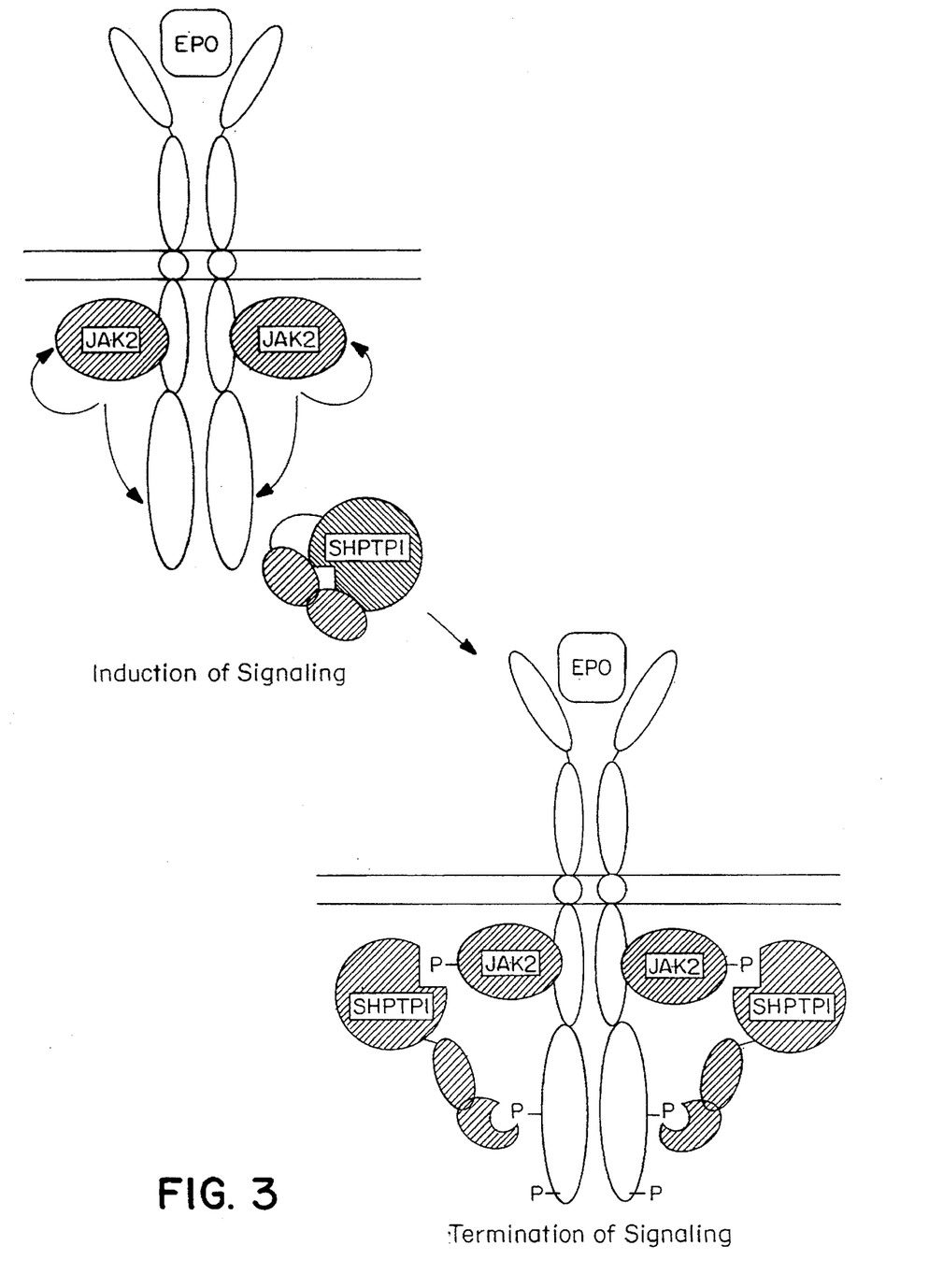
FIG. 3 is an illustration of binding of SH-PTP1 to the tyrosine-phosphorylated EPO-R down-modulating signal transduction by JAK2.

The results described herein suggest a model for regulation of members of the JAK family of protein-tyrosine kinases (FIG. 3). It is hypothesized that SH-PTP1, like SH-PTP2 (Sugimoto, et al., *J Biol Chem* 268:2733–2736 (1993); Dechert, et al., *J Biol Chem* 269:5602–5611 (1994)) is in an inactive conformation in the cytosol until binding of EPO to the EPO-R activates a protein-tyrosine kinase, presumably JAK2, that phosphorylates Y429 of the EPO-R and probably other substrates. Engagement of the SH-PTP1 SH2 domain(s) by the EPO-R both translocates the phosphatase to the receptor-signaling complex and activates the phosphatase activity in close proximity to possible substrates; one such substrate is JAK2. Dephosphorylation of JAK2 leads to termination of its signaling capability and helps set the normal cellular level of EPO sensitivity. Since a phosphotyrosine-containing peptide derived from residue Y429 of the EPO-R specifically activates SH-PTP1, and since overexpression of SH-PTP1 represses growth of a myeloid cell line, therapeutic agents mimicking the activity mediated by this phosphotyrosine peptide could be of therapeutic importance.

Figure 4:
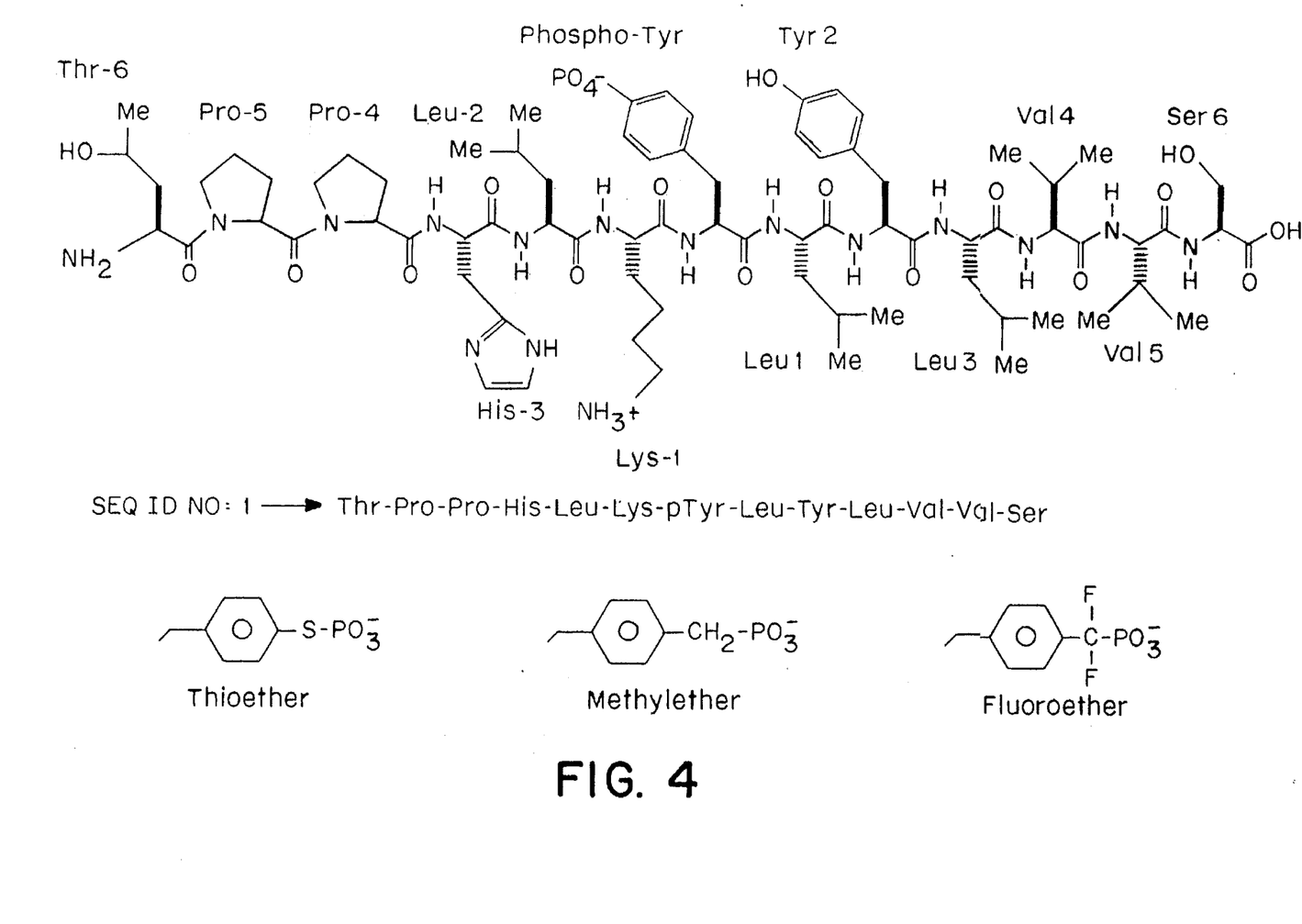
FIG. 4 is the amino acid sequence (SEQ ID NO.: 1) of an EPO receptor peptide which contains the phosphorylated tyrosine 429 SH-PTP1 binding site. Also shown are fluoroether, methylether and thioether groups which can be used to modify one or more amino acids of the peptide.

A 13 amino acid residue synthetic peptide (SEQ ID NO.: 1, FIG. 4) derived from the EPO-R, which contains the phosphorylated tyrosine 429 SH-PTP1 binding site, has also been constructed. Other similar peptides or agents, which bind to SH-PTP1 and activate the phosphatase, such as small organic molecules, can be designed, based on the peptide described herein, and can be produced using known methods (e.g., recombinant DNA methods or synthetic methods). Such peptides or small organic molecules bind SH-PTP1 and activate the phosphatase activity or prevent SH-PTP1 from binding to the EPO-R. The peptides differ from the peptide described herein by deletion, alteration or addition of at least one amino acid residue; for instance, an 11 amino acid residue peptide has been shown to bind SH-PTP1 (Pei et al., *Biochemistry*, 33(51):15483–15493 (1994)). This peptide differs from the peptide of SEQ ID NO.: 1 in that it does not contain the first two amino acid residues. The peptide may be further modified to increase its ability to enter cells and its stability within the cell; for example, at least one amino acid, e.g., phosphorylated tyrosine 429, can be modified by addition of a fluoroether, methylether, or thioether group to prevent hydrolysis in the cell (FIG. 4). Alternatively a small organic molecule which retains the ability to bind SH-PTP1 can be designed with appropriate modifications, e.g., to increase stability or other selected properties.

The invention will be further illustrated by the following non-limiting examples:

Plasmids and Mutagenesis

To convert tyrosine residues to phenylalanines in the cytosolic domain of the EPO-R, point mutations were generated by overlap extension using the polymerase chain reaction (PCR) with synthetic oligonucleotides encoding the desired amino acid substitutions (Higuchi, et al., *Nucleic Acids Res* 16:7351–7367 (1988)).

Parental Ba/F3 cells and Ba/F3 cells expressing wild-type or mutant EPO-Rs (Y429,431F and Y460,464F) were incubated with 100 units EPO/ml for 5 minutes at 37° C. and then lysed. Immunoprecipitates of the lysates with antibodies against EPO-R or SH-PTP1 were analyzed by anti-pTyr immunoblotting. Anti-SH-PTP1 immunoprecipitates of lysates of Ba/F3 cells expressing the wild-type EPO-R were boiled in 50 µl of 1% SDS, diluted tenfold with 1×lysis buffer, and incubated with a mixture of EPO-R antibodies raised against N-and C-terminal EPO-R peptides or preimmune serum. These immunoprecipitates were analyzed by anti-pTyr immunoblotting. To show the equal efficiency of immunoprecipitation the blots were either reprobed with anti-EPO-R antiserum or anti-SH-PTP1 antiserum. The carboxy-terminal truncated EPO-R 1-374 was created by introducing an oligonucleotide that contained a stop codon into the HindIII site at nucleotide position 1221 in the EPO-R cDNA. Mutant EPO-R cDNAs were identified by sequencing using the dideoxynucleotide chain termination method and subcloned into the eukaryotic expression vector pXM-EPO-R (D'Andrea, et al., *Cell* 57:277–285 (1989); Longmore and Lodish, *Cell* 67:1089–1102 (1991)) by ligating the ApaI-EcoR1 fragment of the mutant EPO-R cDNAs into ApaI and EcoR1-cut pXM-EPO-R DNA. The construction of the carboxy-terminal truncated EPO-R mutant (1-441) was described previously (Yoshimura, et al., *PNAS* 87:4139–43 (1990)).

Cell Culture and Transfections

Wild-type or mutant EPO-R cDNAs in pXM were cotransfected with the selectable marker pRc/CMV(neo) into the IL-3 dependent pro-B cell line Ba/F3 or the myeloid cell line 32D by electroporation as described (Skoda, et al., *EMBO J* 12:2645–2653 (1993)). Beginning 24 hours after transfection, pools of G418-resistant cells were selected in 24 well plates (GIBCO) in medium containing 0.6 mg/ml G418 and 10% conditioned medium from the WEJI 3B cell line (WEHI CM) as a source of IL-3. To identify pools of transfected cells expressing an EPO-R, and thus competent to grow in the presence of EPO, neomycin resistant colonies were transferred to medium containing 0.3 U EPO (Arris Pharmaceuticals, Inc.) per ml as the sole growth factor. EPO-responsive cell pools were further characterized by immunoprecipitation and immunoblotting with anti-EPO-R antiserum. Cell pools that showed comparable surface expression of the wt or mutant EPO-Rs were identified by saturation binding of [$^{125}$I] EPO at 4° C. (Hilton, et al., *PNAS* 85:5971–5975 (1988)). Interleukin 3-dependent and EPO-dependent cells were maintained as described previously (Yoshimura, et al., 1990). Briefly, Ba/F3 cells and 32D cells were maintained in RPMI 1640 medium (GIBCO) supplemented with 10% heat inactivated fetal calf serum (Sigma) and 10% WEHI-conditioned medium.

Immunoprecipitations and Immunoblotting

Antibodies directed against the EPO-R were either raised against a peptide corresponding to the C-terminus of the EPO-R (anti-C-EPO-R; Yoshimura, et al., 1990) or against GST-fusion protein containing the EPO-R extracellular domain (anti-EPO-R). The anti-EPO-R antiserum was affinity-purified by expressing the extracellular domain of the EPO-R as a fusion protein with the maltose-binding protein, coupling the purified fusion protein to CNBr activated SEPHAROSE™ 4B (Pharmacia) according to the manufacturer's instructions, applying the crude antiserum to the column, and eluting specifically bound antibodies with 100 mM glycine, pH 2.5.

Populations of Ba/F3 cells expressing wild-type or mutant EPO-Rs were grown to high density ($5 \times 10^5$ cells/ml), washed with RPMI medium, and incubated at a density of $5 \times 10^7$ cells per ml with 100 U EPO/ml for the indicated times. Extracts were directly prepared by the addition of an equal volume of 2x lysis buffer (2% NP-40, 20% glycerol, 300 mM NaCl, 100 mM Tris-HCl (ph 7.4), 100 mM NaF, 2 mM $ZnCl_2$, 2 mM $Na_3VO_4$, 10 µg/ml leupeptin, and 1 mM AEBSF (ICN). For immunoprecipitations the cell extracts (250 µl) were incubated with 2 µg affinity-purified polyclonal rabbit antibodies against human SH-PTP1 (Lorenz, et al., *Mol Cell Biol* 14:1824–1834 (1994)), 1 µl JAK2 antiserum (UBI), or 3 µg affinity-purified antibodies against the EPO-R, as indicated. Immune complexes were recovered by binding to Protein A-SEPHAROSE™ beads (Boehringer Mannheim). Protein-A-bound immunoprecipitates were washed three times with 1x lysis buffer and once with TNE (50 mM Tris-HCl pH 8.0, 150 mM NaCl, 1 mM $Na_3VO_4$, 1 mM $ZnCl_2$ and 1 mM EDTA), and eluted by boiling in SDS sample buffer. Samples were separated on 10% low bias SDS-polyacrylamide gels, transferred to nitrocellulose membranes (Scheicher and Schüll), and incubated with the indicated antiserum in 150 mM NaCl, 10 mM Tris-HCl (pH 8), 1% BSA, and 0.2% Tween-20 for two hours at room temperature. Antibodies used for immunoblotting were a polyclonal rabbit antiserum against SH-PTP1 (Lorenz, et al., 1994; 1 to 1000), affinity purified anti-EPO-R antiserum (1 to 5000), anti-C-EPO-R antiserum (1 to 1000), anti-JAK2 antiserum (1 to 1000) and the monoclonal anti-phosphotyrosine antibody 4G10 (anti-pTyr; a kind gift of B. Drucker, 1 µg per ml). Bound antibodies were detected by incubation with horseradish peroxidase-coupled secondary antibodies (anti-rabbit or anti-mouse as appropriate) (Amersham) and the Dupont/NEN chemiluminescence enhancement system (ECL) as detailed by the manufacturer.

To reprobe immunoblots, filters were incubated in 62.5 mM Tris 6.8/0.1M β-mercaptoethanol/2% SDS for 30 min. at 65° C. and then washed extensively in 10 mM Tris pH 8/150 mM NaCl.

GST-Fusion Proteins

The N-and C-terminal SH2 domains of murine SH-PTP1 were cloned into the EcoRI site of the bacterial expression vector pGEX-2T (Pharmacia). For the N-terminal SE2 domain as well as for the both of the SH2 domains together (N+C), the cDNA fragments corresponding to amino acids 1-121 and 1-220, respectively, were amplified by PCR, using Vent DNA polymerass (NEB) and the following primers: 5'-GCCGGAATTCTCCACATTTTCTGCAGCCAATTC-3' (SEQ ID NO.: 2; 5' primer); 5'-CGGCGAATTCCCGCCTGCCCTCCAGATATGTG-3' (SEQ ID NO.: 3; 3' primer for the N-terminal SH2 domain); and 5'-CGGCGAATTCCTGCGTTTACCCGAGTAGCGTAG-3' (SEQ ID NO.: 4; 3' primer for both SH2 domains (N+C).

Parental Ba/F3 cells or Ba/F3 cells expressing the WT; Y429, 431F; Y431F; or Y460, 464F EPO-Rs were incubated with 100 units EPO/ml for 3 minutes at 37° C. and lysed. The lysates were subjected to immunoprecipitation with an antiserum against the EPO-R. The lysates were incubated with GST-fusion proteins containing both SH-PTP1 SH2 domains or the N-terminal SH2 domain or to GST alone. The immunoprecipitated or complexed proteins were analyzed by SDS-PAGE and anti-pTyr immunoblotting.

The amplified DNA fragments were sequenced by fluorescent dye technology on a 373A DNA sequencer (Applied Biosystems). *E. coli* transformants expressing the GST-SH-PTP1 fusion proteins were induced with 1 mM IPTG (Sigma) at 30° C. for 12 hours, harvested by centrifugation, and lysed as described previously (Songyang, et al., *Cell* 72:767–778 (1993)). Cells were stimulated with 100 units EPO/ml for 5 minutes at 37° C. prior to detergent lysis. GST-fusion proteins bound to glutathione-agarose beads (approximately 1 µg fusion protein per binding reaction) were incubated for three hours at 4° C. with 250 µl lysate, equivalent to $1 \times 10^7$ cells, in a x lysis buffer. After washing the beads several times with lysis buffer, absorbed proteins were eluted and analyzed as described above for immunoprecipitates.

The GST fusion protein of the cytoplasmic domain of the EPO-R was obtained by inserting the cytoplasmic domain of the EPO-R into pGEX-2T (Pharmacia). To do this, the cytoplasmic domain of the EPO-R was amplified by PCR, simultaneously introducing a BclI restriction side at nucleotide position 841 in the EPO-R-cDNA. The BclI-EcoRI digested PCR-product was ligated to the BamHI-EcoRI digested pGEX-2T and transfected into *E. coli*. Transformants expressing the fusion protein were identified by immunoblotting with anti C-EPO-R. The fusion protein was induced and purified as above, eluted from glutathione agarose beads (Sigma) with elution buffer (75 mM Tris-HCl pH 8.0, 150 mM NaCl, 5 mM DTT and 20 mM reduced glutathione) and used directly in kinase assays.

Baculovirus Constructs and Infection of Insect Cells

JAK2, SH-PTP1 and SH-PTP2 were expressed in insect cells by infection with recombinant baculoviruses. Viruses encoding SH-PTP1 and SH-PTP2 can also be constructed and used to express SH-PTP1 and SH-PTP2. For insertion of JAK2 DNA into the insect cell transfer vector pVL 1393 (Pharmingen), the cDNA encoding JAK2 was amplified by PCR from prepro-B cell first strand cDNA. Three pieces of JAK2 cDNA—corresponding to nucleotides 94–1200, 1170–2580 and 2242–3483 of the published sequence (Silvennoinen, et al., 1993)—were generated and subcloned into SpeI-and ApaI-digested pBluescript SK+DNA (Stratagene) using unique SpeI and ApaI restriction sides introduced by PCR at the ends of each fragment. The complete JAK2 coding sequence was reassembled, and excised from pBluescript by digestion with NotI and ApaI, and the single-stranded ApaI end was filled in. pVL 1393 DNA was digested with NotI and BgIII, and the BgIII end was filled in with Klenow. The digested JAK2 and pVL 1393 DNAs were then ligated. All products were verified by automated sequencing.

Recombinant baculoviruses were prepared using the BaculoGold kit (Pharmingen) according to the directions of the manufacturer. Viruses were plaque-purified prior to use in protein production. For co-infection experiments, $3 \times 10^6$ Sf9 insect cells were simultaneously infected with JAK2 virus (at an m.o.i. of 1-3). Cells were harvested at 72 hours after infection and cell pellets were stored frozen prior to lysis.

Cell pellets were lysed in 250 μl×lysis buffer (described above) and cleared of debris by centrifugation. Cell lysates were either analyzed directly (20 μl per lane; equivalent to $1 \times 10^5$ cells) or used for immunoprecipitations. For each immunoprecipitation, 250 μl lysate (equivalent to $3 \times 10^6$ cells) were incubated with 2.5 μl anti-JAK2 antiserum (UBI) and 50 μl Protein-A SEPHAROSE™. To assay for kinase activity the recovered immunocomplexes were washed as described above for immunoprecipitations and incubated in 100 μl kinase buffer (40 mM PIPES pH 6.8, 10 mM $MnCl_2$ and 100 μM ATP) for 10 min. at 30° C. Approximately 5 μg of a GST-EPO-R fusion protein was added as exogenous substrate to each reaction.

Sf9 cells were infected with wild type parental baculovirus, with baculovirus encoding JAK2, with baculoviruses encoding JAK2 and SH-PTP1, or with baculoviruses encoding JAK2 and SH-PTP2. Total cell lysates were analyzed by SDS-PAGE and Coomassie blue staining or were transferred to nitrocellulose membrane and immunoblotted with anti-pTyr antibody. The immunoblott was reprobed with anti-JAK2 antiserum to show comparable expression of JAK2 in the samples. JAK2 protein expressed in Sf9 insect cells is not visualized by Coomassie blue staining.

The extent of phosphorylation of JAK2 expressed in insect cells correlates with its ability to phosphorylate an exogenous substrate. Sf9 cells were infected with wild-type baculovirus, with baculovirus encoding JAK2, with baculoviruses encoding JAK2 and SH-PTP1, or with baculoviruses encoding JAK2 and SH-PTP2. Immunoprecipitates from lysates of $3 \times 10^6$ infected cells with the anti-JAK2 antiserum were subjected to an in vitro kinase assay using a GST-EPO-R-cytosolic domain fusion protein of as an exogenous substrate. The reaction products were analyzed by immunoblotting with anti-pTyr antibody. To show that all reactions contained equal amounts of GST-EPO-R substrate, the blot was reprobed with the anti-C-EPO-R antiserum and to show equal amounts of JAK2 in the reactions the blot was reprobed with the anti-JAK2 antiserum.

Proliferation Assay

Proliferation assays were performed in 96 well plates with 200 μl/well. $5 \times 10^4$ 32D cells/ml were seeded in the presence of indicated amounts of cytokines (EPO 0—5 units/ml; IL3 0–100 units/ml). After 48 hours, 1 μCi 3H-Thymidine (DuPont NEN)/well was added for another 3 hours. The labeled cells were then harvested by a 96 well plate harvester (Scantron Instruments Inc.) and the amount of radioactively labeled DNA was quantitated in a scintillation counter.

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. A peptide which binds to the src homology 2 domains of protein tyrosine phpsphatase SH-PTP1, said peptide consisting of SEQ ID NO.: 1.

2. The peptide of claim 1, wherein at least one amino acid residue is modified by addition of a substituent selected from the group consisting of:

a) a fluoroether;

b) a methylether; and c) a thioether.

* * * * *

UNITED STATES PATENT AND TRADEMARK OFFICE
CERTIFICATE OF CORRECTION

PATENT NO. : 5,659,012
DATED : August 19, 1997
INVENTOR(S) : Ursula Klingmüller, Stephen Michnick and Harvey F. Lodish It is certified that error appears in the above-identified patent and that said Letters Patent is hereby corrected as shown below:

On the title page,

[54]   Title:   Delete "$SH_2$" and insert --SH2--.

[75]   Inventors:  Delete "Benjamin G. Neel, Wayland, Mass; Ulrike Lorenz, Boston, Mass."

Signed and Sealed this

Eleventh Day of May, 1999

Attest:

Q. TODD DICKINSON

Attesting Officer     Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Modified-site
        ( B ) LOCATION: 7
        ( D ) OTHER INFORMATION: /product="Phosphorylated Tyrosine"

( x i ) SEQUENCE DESCRIPTION: SEQ ID NO:1:

Thr Pro Pro His Leu Lys Tyr Leu Tyr Leu Val Val Ser
    1                5                                      10

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single

```
        ( D ) TOPOLOGY: linear ( i i ) MOLECULE TYPE: DNA (genomic)

( x i ) SEQUENCE DESCRIPTION: SEQ ID NO:2:

GCCGGAATTC  TCCACATTTT  CTGCAGCCAA  TTC                    33

( 2 ) INFORMATION FOR SEQ ID NO:3:

( i ) SEQUENCE CHARACTERISTICS:
                ( A ) LENGTH: 32 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:3:

CGGCGAATTC  CCGCCTGCCC  TCCAGATATG  TG                     32

( 2 ) INFORMATION FOR SEQ ID NO:4:

( i ) SEQUENCE CHARACTERISTICS:
                ( A ) LENGTH: 33 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:4:

CGGCGAATTC  CTGCGTTTAC  CCGAGTAGCG  TAG                    33
```